United States Patent
Spriggs et al.

(10) Patent No.: US 9,869,625 B2
(45) Date of Patent: Jan. 16, 2018

(54) APPARATUS AND METHOD FOR MEASURING PARTICLE SIZE DISTRIBUTION BY LIGHT SCATTERING

(75) Inventors: David Michael Spriggs, Malvern (GB); Duncan Stephenson, Malvern (GB)

(73) Assignee: Malvern Instruments Limited, Malvern (GB)

(*) Notice: Subject to any disclaimer, the term of this patent is extended or adjusted under 35 U.S.C. 154(b) by 431 days.

(21) Appl. No.: 14/345,073

(22) PCT Filed: Sep. 11, 2012

(86) PCT No.: PCT/GB2012/052229
§ 371 (c)(1),
(2), (4) Date: Jan. 7, 2015

(87) PCT Pub. No.: WO2013/038160
PCT Pub. Date: Mar. 21, 2013

(65) Prior Publication Data
US 2015/0138550 A1    May 21, 2015

Related U.S. Application Data
(60) Provisional application No. 61/534,851, filed on Sep. 14, 2011.

(30) Foreign Application Priority Data
May 10, 2012   (GB) .................................. 1208181.6

(51) Int. Cl.
*G01N 15/02* (2006.01)
*G01N 21/47* (2006.01)
*G01N 21/49* (2006.01)

(52) U.S. Cl.
CPC ..... *G01N 15/0205* (2013.01); *G01N 15/0211* (2013.01); *G01N 21/47* (2013.01);
(Continued)

(58) Field of Classification Search
USPC .................................................. 356/335–344
See application file for complete search history.

(56) References Cited

U.S. PATENT DOCUMENTS

| | | | | |
|---|---|---|---|---|
| 4,361,403 A | * | 11/1982 | Loos | G01N 15/0211 250/574 |
| 4,881,231 A | * | 11/1989 | Jain | H01S 3/1062 372/18 |

(Continued)

FOREIGN PATENT DOCUMENTS

| | | |
|---|---|---|
| CN | 101118210 | 8/2007 |
| CN | 201935855 | 1/2011 |

(Continued)

OTHER PUBLICATIONS

Office Action (Japanese Patent Application Serial No. 2014530309), dated May 31, 2016 (translation).

*Primary Examiner* — Tri Ton
*Assistant Examiner* — Jarreas C Underwood
(74) *Attorney, Agent, or Firm* — Kristofer E. Elbing

(57) ABSTRACT

Apparatus (100) for measuring particle size distribution by light scattering comprises a blue LED (102) and a 633 nm helium neon laser (104). Light output from the LED and laser is separately passed or reflected by a dichroic element (116) onto a common path through a sample cell (122) containing a sample, the particle size distribution of which is to be measured. Light scattered from the sample cell is detected by one or more detectors (112B-H). Light transmitted by the sample cell is detected by detectors 112A, 112J. Output signals from one or more of the detectors are passed to a computation unit (114) which calculates particle size distribution. A small percentage of light from the blue LED is reflected by the dichroic element to a detector (110). Similarly, a small percentage of light from the laser is passed by the dichroic element to the detector. Output signals from
(Continued)

Figure 1:
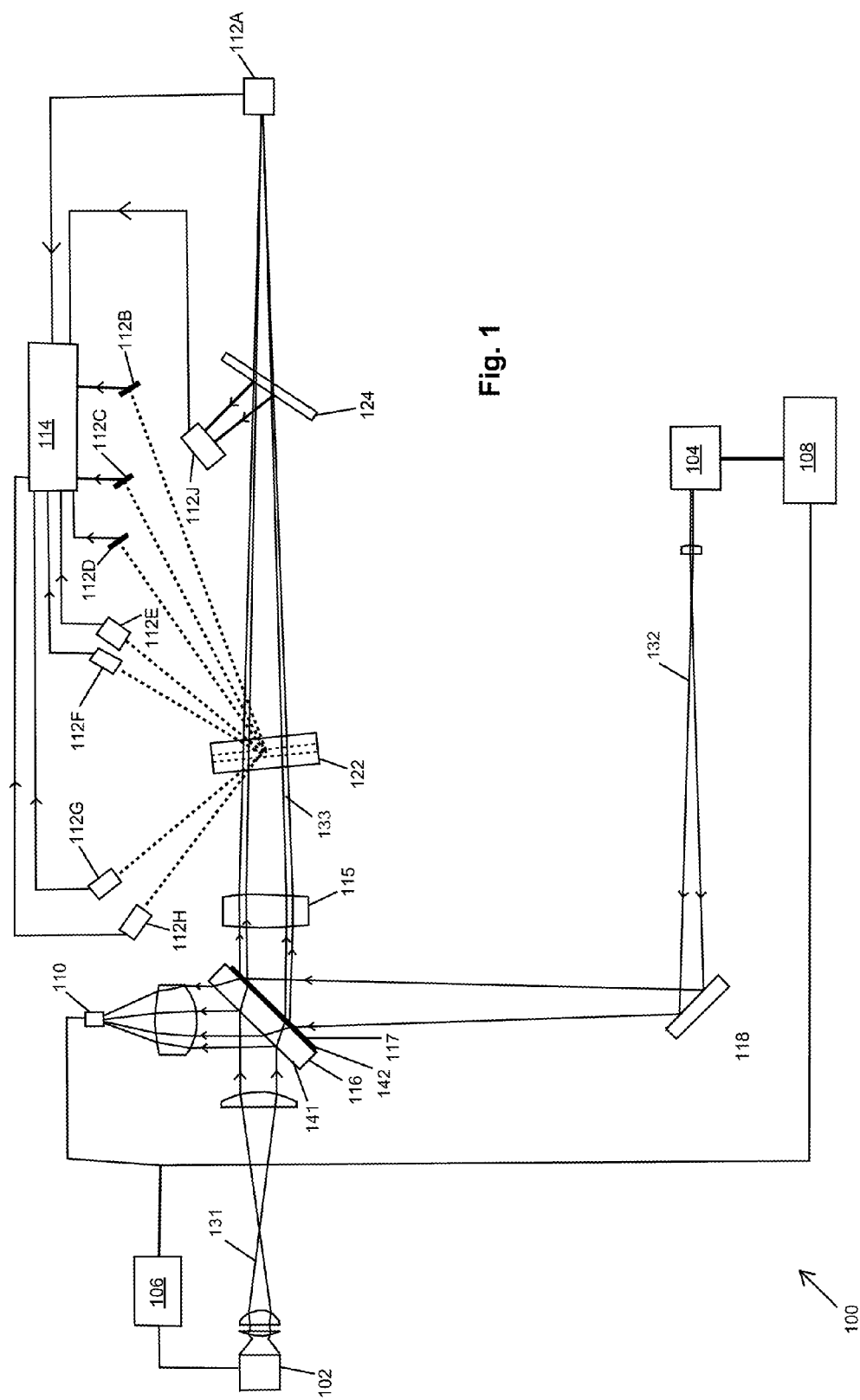

the detector are fed back to control units (106, 108) to stabilize the output power of the LED and laser.

27 Claims, 4 Drawing Sheets

(52) U.S. Cl.
CPC ....... *G01N 21/49* (2013.01); *G01N 2201/062* (2013.01); *G01N 2201/06113* (2013.01)

(56) References Cited

U.S. PATENT DOCUMENTS

| | | | | |
|---|---|---|---|---|
| 4,938,593 | A * | 7/1990 | Morris | G01N 21/171 356/344 |
| 4,953,978 | A * | 9/1990 | Bott | G01N 15/0211 356/336 |
| 4,957,363 | A | 9/1990 | Takeda | |
| 5,135,306 | A * | 8/1992 | Kanebako | G01N 15/0205 250/574 |
| 5,416,580 | A | 5/1995 | Trainer | |
| 5,469,251 | A * | 11/1995 | Kosaka | G01N 15/1475 356/317 |
| 5,475,235 | A * | 12/1995 | Phillips | H01S 5/042 250/574 |
| 5,530,551 | A * | 6/1996 | Cantrall | G01B 11/105 356/335 |
| 5,831,730 | A * | 11/1998 | Traina | G01N 15/0205 250/564 |
| 6,177,994 | B1 * | 1/2001 | Watson | G01N 15/0211 356/337 |
| 6,246,892 | B1 * | 6/2001 | Chance | A61B 5/0075 600/310 |
| 6,618,144 | B1 * | 9/2003 | Reed | G01N 15/0211 356/336 |
| 6,858,104 | B2 * | 2/2005 | Flanagan | B23K 26/03 156/272.8 |
| 7,339,661 | B2 * | 3/2008 | Korngut | G01N 21/47 250/234 |
| 7,433,053 | B2 * | 10/2008 | Some | G01N 21/47 356/512 |
| 7,869,038 | B2 * | 1/2011 | Jones | G01N 15/0205 356/335 |
| 8,681,331 | B2 * | 3/2014 | Xie | G01N 21/171 356/337 |
| 2008/0285032 | A1 | 11/2008 | Ohkubo | |
| 2009/0122313 | A1 | 5/2009 | Jones | |
| 2009/0323061 | A1 * | 12/2009 | Novotny | G01N 15/1456 356/336 |

FOREIGN PATENT DOCUMENTS

| | | |
|---|---|---|
| CN | 102175587 | 9/2011 |
| EP | 0485817 | 11/1999 |
| EP | 1884762 | 8/2006 |
| EP | 2163883 | 3/2010 |
| GB | 2340936 | 3/2000 |
| GB | 2346444 | 9/2000 |
| JP | 2000097841 | 4/2000 |
| JP | 20000146814 | 5/2000 |
| JP | 20050888512 | 4/2005 |
| JP | 2006134534 | 5/2006 |
| JP | 2014530309 | 11/2014 |
| WO | 0077489 | 12/2000 |

* cited by examiner

APPARATUS AND METHOD FOR MEASURING PARTICLE SIZE DISTRIBUTION BY LIGHT SCATTERING

This application is a US National Stage counterpart of PCT/GB2012/052229, filed Sep. 11, 2012, and claims priority to provisional application No. 61/534,851, filed Sep. 11, 2011.

The invention relates to apparatus and methods for measuring particle size distribution by light scattering.

Methods and apparatus for measuring particle size distribution for a sample by monitoring light scattered by the sample are known. In some such techniques, light scattered at two different wavelengths is monitored to extend the range of particles sizes that can be measured and/or to improve resolution. For example, in the method and apparatus described in European Patent 0 992 785 light from a blue laser diode or blue LED is used to make scattering measurements in addition to taking scattering measurements using a laser having an output of longer wavelength, for example a helium-neon laser, to enhance detection and resolution for sub-micron particle sizes.

In order to obtain scattering measurements at two different wavelengths, the optical output beams from two suitable light sources are generally multiplexed onto a common path through a sample containing particles, or at least some arrangement is provided so that each beam may impinge on the sample at respective time along the same path. A beam-splitter or dichroic mirror can be used to achieve this function. Means are normally provided for detecting the beams prior to interaction with the sample so that fluctuations in the output powers of the light sources can be corrected by adjusting the light sources, or so that such fluctuations can be taken into account when calculating particle size distribution.

A first aspect of the present invention provides apparatus for measuring particle size distribution for a sample by light scattering, the apparatus comprising light-generating means for generating first and second beams of light having first and second wavelengths respectively, a dichroic element arranged to direct most of the power of the first and second beams onto a common path by transmission and reflection of the first and second beams respectively at the dichroic element, and wherein the apparatus further comprises a first detector arranged to detect a portion of the first beam reflected by the dichroic element.

In apparatus of the invention, the power of the first beam may be monitored by detecting the portion of the first beam which is reflected by the dichroic mirror to the first detector. This obviates the need for more complex arrangements for monitoring the power of the first beam as incident on the sample. Apparatus of the invention is therefore simpler and cheaper than apparatus of the prior art having the same functionality, and utilises light energy that would other be wasted. By reducing the number of optical elements compared to apparatus of the prior art, stray reflections and unwanted scattering within the apparatus is reduced, thus improving the signal-to-noise ratio for light scattered by the sample and subsequently detected within the apparatus. This is particularly important in the detection of light backscattered by the sample.

The apparatus may comprise a control system for controlling the power of the first beam, the control system being arranged to receive an output signal from the first detector and to adjust the power of the first beam in response thereto. For example if the first beam is provided by a laser, the control system may be arranged to increase the pumping rate of the laser if power detected by the first detector decreases, and to reduce the pumping rate if the power detected by the first detector increases, in order to stabilise the power of the first beam.

The apparatus may comprise a computation unit arranged to receive a signal from the first detector and to calculate particle size distribution of the sample based in part on this signal. In this case the computation unit is arranged to take into account fluctuations in the power of the first beam in calculating the particle size distribution for particles in the sample.

The first detector may be arranged to detect a portion of the second beam transmitted by the dichroic element, in addition to being arranged to detect a portion of the first beam reflected by the dichroic element. This allows the powers of both the first and second beams to be monitored and used either to stabilise their respective powers or to be taken into account to determine particle size distribution for the sample. The use of a common dichroic element to allow the detector to detect both the first and second beams as well as directing the beams onto a common path reduces the number of optical components and thereby makes the apparatus simpler, as well as reducing any scattering that is inevitably introduced by each additional optical element.

Alternatively, in order to additionally monitor the power of the second beam, the apparatus may further comprise a second detector and an optical element arranged to transmit substantially all the power of the second beam to the dichroic element and to reflect a portion of the power of the second beam to the second detector.

The first wavelength may be shorter than the second wavelength, for example the first beam may be generated by a blue laser diode or blue LED, and the second beam may be generated by a 633 nm helium-neon laser or a red LED.

The dichroic element may be glass element having substantially plane parallel sides, one of which carries a dichroic coating. Preferably, the rate of change of reflectivity of the dielectric coating as a function of wavelength at the first wavelength is substantially zero so that the performance of the dichroic element is insensitive to variations in the first wavelength that may occur when the light-generating means is first switched on. For a typical standard dichroic coating, the transmission for red light is around 0.2%, however more preferably the transmission of the dichroic coating at the second wavelength is between 2% and 10%.

The dichroic element may be comprised in a dust-free housing together with one or more other optical elements for delivery of light to a sample within the apparatus. This reduces unwanted scattering between the light source and the sample.

A second aspect of the invention provides a method of measuring particle size distribution for a sample comprising the steps of:
(i) generating first and second beams of light having first and second wavelengths respectively; and
(ii) using a dichroic element to direct most of the power of the first and second beams onto a common path by transmission and reflection of the first and second beams respectively at the dichroic element;
wherein the method comprises the step of using a first detector to detect a portion of the first beam reflected by the dichroic element and generate a corresponding output signal.

Another aspect of the invention provides apparatus for measuring particle-size distribution of a sample by light-scattering, the apparatus comprising light-generating means for generating first and second beams of light having first and second wavelengths respectively, the first wavelength being shorter than the second wavelength, means for directing respective portions of the two beams along a common path to a converging optic arranged to provide converging light at the first and second wavelengths to a sample cell, and a focal plane detector arranged to detect light of the second wavelength transmitted by the sample cell, and wherein the apparatus further comprises an optical component disposed between the sample cell and the focal plane detector and arranged to reflect light of the first wavelength to an optical detector.

Embodiments of the invention are described below with reference to the accompanying drawings in which FIGS. 1 to 4 show respective apparatus for measuring particle size distribution.

Referring to FIG. 1, an exemplary apparatus 100 for measuring particle size distribution comprises a blue LED 102, a 633 nm helium neon (HeNe) laser 104, control units 106, 108, a dichroic element 116 having a dichroic coating 117 on one side thereof, a sample cell 122 containing a sample of particles the size distribution of which is to be measured, an optical detector 110, a detection arrangement having detectors 112A-J and a computation unit 114. The illustrated exemplary embodiments are schematic and simplified representations of apparatus suitable for carrying out the invention. Further components such as additional lenses and mirrors to those shown in the accompanying drawings may be incorporated without departing from the scope of the invention.

The apparatus 100 is typically operated using the blue LED 102 and HeNe laser 104 separately to obtain light scattering measurements from which the particle size distribution for the sample in the sample cell 122 may be deduced by the computation unit 114. A first beam 131 of blue light from the blue LED 102 is largely passed by the dichroic element 116 and passes to the sample cell 122 via a focussing optic 115 where it is scattered and subsequently detected by one or more of detectors 112B-H. A few percent of the light from the blue LED is reflected by a first face 141 of the dichroic element 116 and passes to the detector 110. A second beam 132 of red light output by the HeNe laser 104 is reflected by a mirror 118 and is incident on a second opposing face 142 of the dichroic element 116. A few percent of the red light passes through the dichroic element 116 to the detector 110; the remainder is reflected by the second face 142 of the dichroic element 116 towards the sample cell 122 where it is scattered and detected by one or more of the detectors 112B-H. The first beam 131 of blue light from the LED 102 and the second beam 132 of red light from the HeNe laser 104 thus follow a common path 133 from the second face 142 of the dichroic element 116 to the sample cell 122. Signals from the individual detectors 112B-H of the detection arrangement (resulting from the detection of scattered light) are passed to computation unit 114 arranged to calculate particle size distribution for particle in the sample cell 122 in response thereto. Blue light transmitted by the sample cell 122 is detected by detector 112J. Red light transmitted by the sample cell 122 is reflected by a reflective element 124 and detected by a detector 112A. Output signals from the detectors 112A, 112J are also passed to computation unit 114 and used in the calculation of particle size distribution for sample in the sample cell 122.

Output from the detector 110 is passed to control units 106 and 108 which operate to stabilise the output powers of the LED 102 and HeNe laser 104. (In alternative embodiment, only the output power of the LED 102 is controlled.) If the power detected by the detector 110 decreases, the relevant control unit 106 or 108 operates to increase the output power of the LED 102 or laser 104. Similarly if the power detected by the detector 110 increases, the relevant control unit 106 or 108 operates to reduce the output power of the LED 102 or HeNe laser 104. By using the blue light reflected by the first surface 141 of the dichroic element 116 and the red light passed by the dichroic element 116 to monitor the output powers the LED 102 and laser 104, the need for more complex arrangements to monitor beam power incident on the sample is avoided. Also, such light energy is not simply wasted, as in the prior art, and the number of optical elements in the apparatus 100 is reduced, reducing unwanted scattering and stray reflections and improving the signal-to-noise ratio in light scattered by the sample and detected by the detectors 112B-H.

The computation unit 114 is programmed to include steady-state output power values for the LED 102 and HeNe laser 108 which are fixed by the control units 106, 108.

Figure 2:
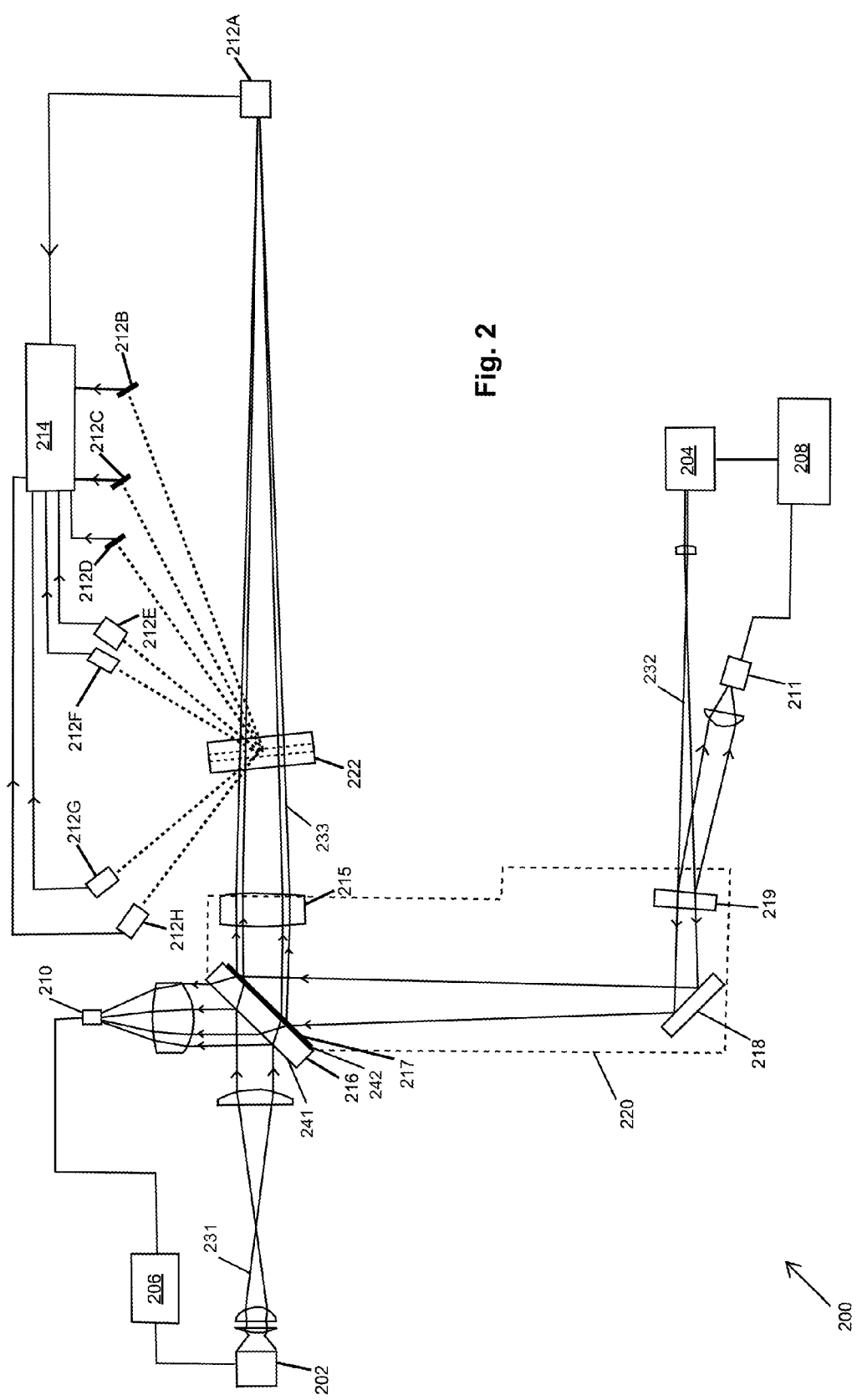

FIG. 2 shows a second example apparatus 200 of the invention for measuring particle size distribution. Parts of the apparatus 200 corresponding to parts of the apparatus 100 of FIG. 1 are labelled using reference signs differing by 100 from reference signs used to label the corresponding parts in FIG. 1. A first beam 231 of light from a blue LED 202 and a HeNe laser 204 may be coupled onto a common path 233 through a sample cell 222 containing a sample of particles the size distribution of which is to be measured. Dichroic element 216 carries a standard dichroic coating 217 which transmits 0.2% of the power incident from the HeNe laser 204 to detector 210. The apparatus 200 includes a reflective element 219 which reflects a few percent of the output power of the HeNe laser 204 to a second detector 211. A few percent of the output power of the blue LED 202 is reflected by dichroic element 216 to a first detector 210. The output powers of the first beam 231 from the LED 202 and the second beam 232 from the HeNe laser 204 are stabilised by control units 206, 208 in response to output signals from the first 210 and second 211 detectors respectively. Both blue and red light transmitted by the sample cell 222 is detected by detector 212A. Light of both wavelengths scattered by the sample in the sample cell 222 is detected by one or more of detectors 212B-H. Output signals from detectors 212A-H are passed to computation unit 214 which is programmed to include the steady-state values of the output powers of the LED 102 and HeNe laser 104 as fixed by control units 204, 206.

Dichroic element 216 is integrated into a dust-free housing 220 together with mirror 218, reflective element 219 and focussing optic 215. The dust-free housing 220 reduces or eliminates scattering of light between the LED 202 and HeNe laser 204 and the sample cell 222.

Figure 3:
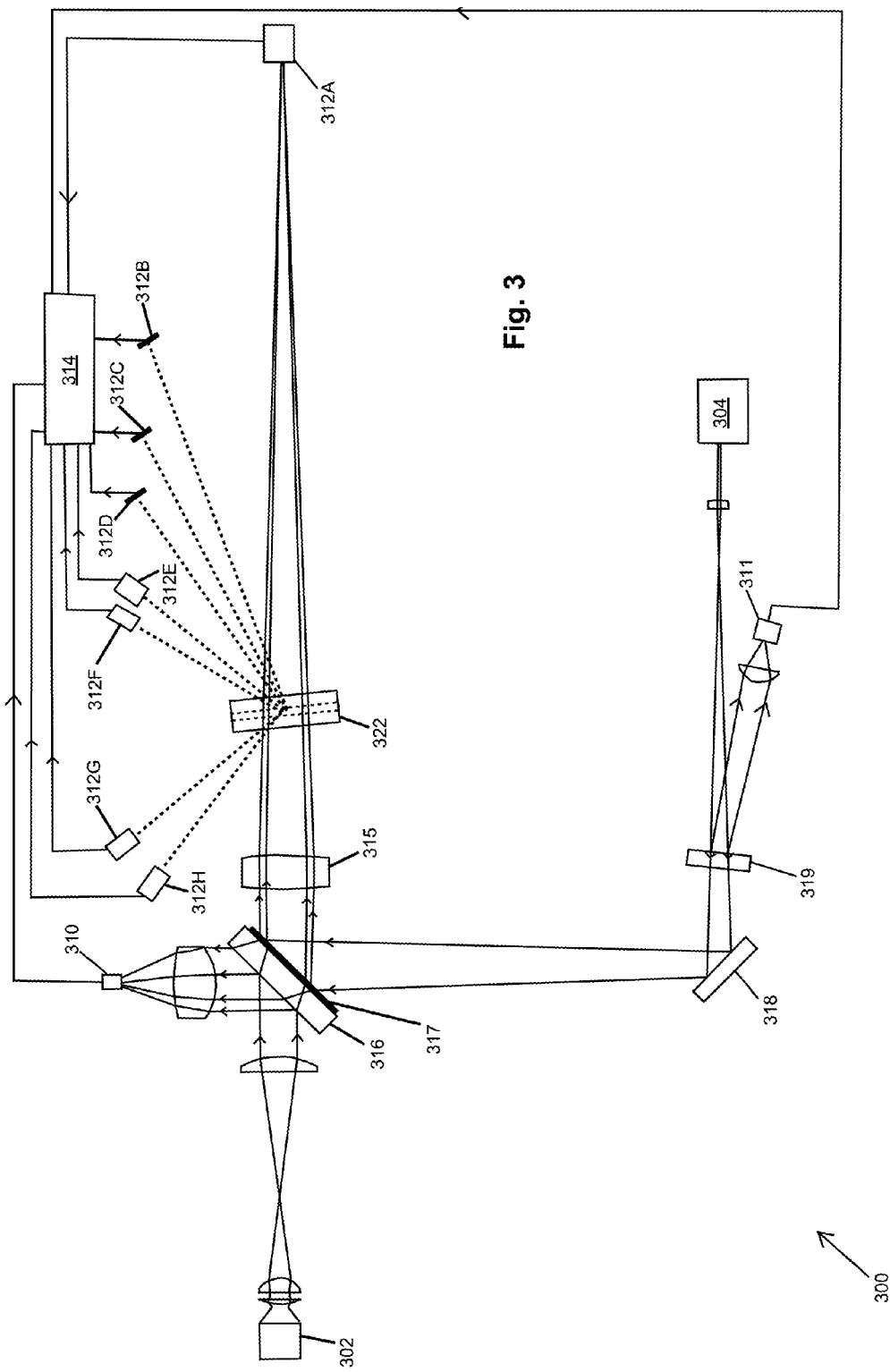

FIG. 3 shows a third example apparatus 300 of the invention. Parts of the apparatus 200 corresponding to parts of the apparatus 100 of FIG. 1 are labelled using reference signs differing by 200 from reference signs used to label the corresponding parts in FIG. 1. The apparatus 300 is similar to the apparatus 200 of FIG. 2 in that dichroic coating 317 is a standard dichroic coating and in that first 310 and second 311 detectors are provided to monitor the output powers of the LED 302 and HeNe laser 311. Output from the first 310 and second 311 detectors is passed to the computation unit 314 together with output from detectors 312A-H to allow computation of particle size distribution for the sample within the sample cell 322. Detector 312A detects both blue and red light transmitted by sample cell 322.

Figure 4:
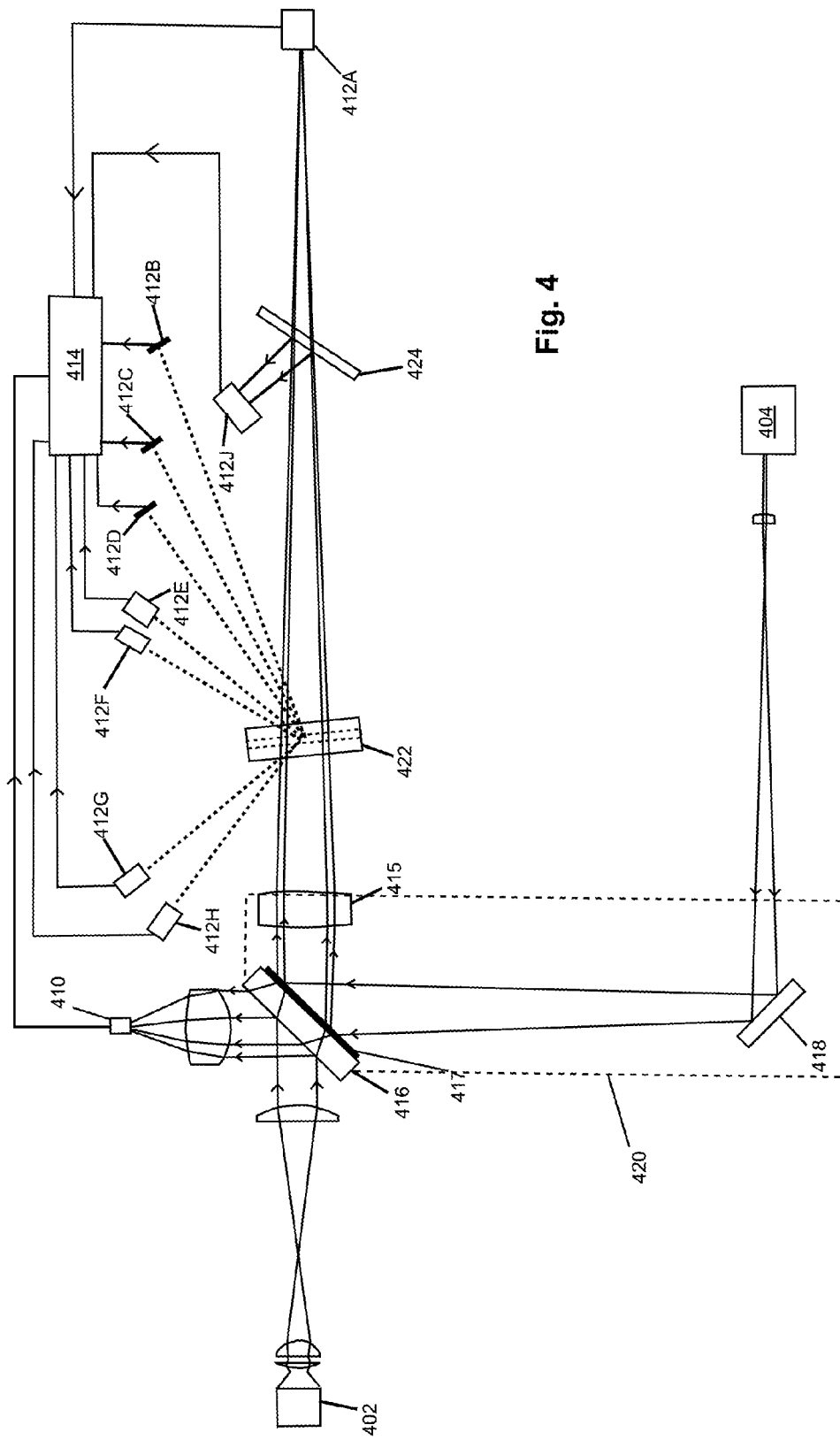

FIG. 4 shows a fourth example apparatus 400 of the invention. Parts of the apparatus 400 corresponding to parts of the apparatus 100 of FIG. 1 are labelled using reference signs differing by 300 from reference signs used to label the corresponding parts in FIG. 1. The apparatus comprises a dichroic element 416 having a custom dichroic coating 417 which passes 5% of the light from HeNe laser 404. A single detector 410 is used to monitor the output powers of blue LED 402 and HeNe laser 404. Output signals from the detector 410 are passed to a computation unit 414 together with output signals from detectors 412A-J to allow computation of particle size distribution of a sample within sample cell 422. Detector 412J detects blue light transmitted by sample cell 422. Red light transmitted by sample cell 422 is reflected to detector 412A.

Dichroic element 416 is comprised in a dust-free housing 420 together with mirror 418 and focussing optic 415 to reduce unwanted scattering by dust between LED 402 and sample cell 422, and between laser 404 and sample cell 422.

Other embodiments are intentionally within the scope of the invention as defined by the appended claims.

The invention claimed is:

1. Apparatus for measuring particle size distribution of a sample by light scattering, the apparatus comprising a first source for generating a first beam of light having a first wavelength and a second source for generating a second beam of light having a second wavelength, a dichroic element arranged to direct most of the power of the first and second beams onto a common path through the sample by transmission and reflection of the first and second beams respectively at the dichroic element, wherein the apparatus further comprises a first detector arranged to detect a portion of the first beam reflected by the dichroic element before it is directed onto the common path, and further comprising a control system for controlling the power of the first beam and wherein said control system is arranged to receive an output signal from the first detector and to adjust the power of the first beam in response thereto.

2. Apparatus according to claim 1 comprising a computation unit arranged to receive a signal from a detector arranged to receive a portion of the first or second beams from the common path and to calculate particle size distribution of the sample based in part on the signal.

3. Apparatus according to claim 1 wherein the first detector is arranged to detect a portion of the second beam transmitted by the dichroic element.

4. Apparatus according to claim 1 further comprising a second detector and an optical element arranged to transmit most of the power of the second beam to the dichroic element and to reflect a portion of the power of the second beam to the second detector.

5. Apparatus according to claim 3 further comprising a control system for controlling the power of the first and second beams and wherein said control system is arranged to receive an output signal from at least the first detector, and to adjust the powers of the first and second beams in response thereto.

6. Apparatus according to claim 3 comprising a computation unit arranged to receive an output signal from at least the first detector, and to calculate particle size distribution of the sample based in part on said output signal or output signals.

7. Apparatus according to claim 1 wherein the first wavelength is shorter than the second wavelength.

8. Apparatus according to claim 7 wherein the first source comprises a blue laser diode or blue LED for generating the first beam, and the second source comprises a helium-neon laser or a red LED for generating the second beam.

9. Apparatus according to claim 7 wherein the dichroic element is a glass optical element having substantially plane parallel sides one of which carries a dichroic coating.

10. Apparatus according to claim 9 wherein the rate of change of reflectivity of the dichroic coating as a function of wavelength at the first wavelength is substantially zero.

11. Apparatus according to claim 9 wherein the transmission $T_{\lambda,2}$ of the dichroic coating at the second wavelength is in the range $2\% \leq T_{\lambda,2} \leq 10\%$.

12. Apparatus according to claim 1 wherein the dichroic element is comprised in a dust-free housing together with one or more other optical elements for delivery of light to a sample within the apparatus.

13. A method of measuring particle size distribution for a sample comprising the steps of:
 (i) generating first and second beams of light having first and second wavelengths respectively; and
 (ii) using a dichroic element to direct most of the power of the first and second beams onto a common path through the sample by transmission and reflection of the first and second beams respectively at the dichroic element;
 wherein the method comprises the step of using a first detector to detect a portion of the first beam reflected by the dichroic element and generate a corresponding output signal.

14. Apparatus for measuring particle size distribution of a sample by light scattering, the apparatus comprising: a first source for generating a first beam of light having a first wavelength and a second source for generating a second beam of light having a second wavelength, a dichroic element arranged to direct most of the power of the first and second beams onto a common path by transmission and reflection of the first and second beams respectively at the dichroic element, and wherein the apparatus further comprises a first detector arranged to detect a portion of the first beam reflected by the dichroic element, and a reflective element arranged to reflect the first beam after transmission through the sample to a detector and to transmit the second beam after transmission through the sample to a further detector.

15. Apparatus according to claim 14 comprising a computation unit arranged to receive a signal from a detector arranged to receive a portion of the first or second beams from the common path and to calculate particle size distribution of the sample based in part on the signal.

16. Apparatus according to claim 14 wherein the first detector is arranged to detect a portion of the second beam transmitted by the dichroic element.

17. Apparatus according to claim 14 further comprising a second detector and an optical element arranged to transmit most of the power of the second beam to the dichroic element and to reflect a portion of the power of the second beam to the second detector.

18. Apparatus according to claim 17 further comprising a control system for controlling the power of the first and second beams and wherein said control system is arranged to receive an output signal from at least the first detector, and to adjust the powers of the first and second beams in response thereto.

19. Apparatus according to claim 17 comprising a computation unit arranged to receive an output signal from at least the first detector, and to calculate particle size distribution of the sample based in part on said output signal or output signals.

20. Apparatus according to claim 14 wherein the first wavelength is shorter than the second wavelength.

21. Apparatus according to claim 20 wherein the first source comprises a blue laser diode or blue LED for generating the first beam, and the second source comprises a helium-neon laser or a red LED for generating the second beam.

22. Apparatus according to claim 20 wherein the dichroic element is a glass optical element having substantially plane parallel sides one of which carries a dichroic coating.

23. Apparatus according to claim 22 wherein the rate of change of reflectivity of the dichroic coating as a function of wavelength at the first wavelength is substantially zero.

24. Apparatus according to claim 22 wherein the transmission $T_{\lambda 2}$ of the dichroic coating at the second wavelength is in the range $2\% \leq T_{\lambda 2} \leq 10\%$.

25. Apparatus according to claim 14 wherein the dichroic element is comprised in a dust-free housing together with one or more other optical elements for delivery of light to a sample within the apparatus.

26. Apparatus according to claim 1 wherein the dichroic element is a glass element having a dichroic coating on one side, which reflects the first and second beams onto the common path and wherein the portion of the first beam detected by the first detector passes through the dichroic coating and the glass element.

27. Apparatus according to claim 14 wherein the dichroic element is a glass element having a dichroic coating on one side, which reflects the first and second beams onto the common path and wherein the portion of the first beam detected by the first detector passes through the dichroic coating and the glass element.

* * * * *